United States Patent [19]

Miller et al.

[11] Patent Number: 4,975,855

[45] Date of Patent: Dec. 4, 1990

[54] SHAFT CRACK DETECTION METHOD

[75] Inventors: William H. Miller, Albany, N.Y.; Warren R. Brook, Medford, N.J.

[73] Assignee: REM Technologies, Inc., Albany, N.Y.

[21] Appl. No.: 323,313

[22] Filed: Mar. 14, 1989

[51] Int. Cl.$^5$ .................. G01N 27/82; G01R 33/12
[52] U.S. Cl. .................. 364/507; 364/551.02; 73/581; 73/622; 340/680
[58] Field of Search .......... 364/507, 508, 550, 551.02; 340/679, 680, 683; 73/579, 581, 659, 660, 622

[56] References Cited

U.S. PATENT DOCUMENTS

| | | | |
|---|---|---|---|
| 3,411,134 | 11/1968 | Lloyd | 73/67.2 |
| 4,195,528 | 4/1980 | Takahashi | 73/579 |
| 4,342,229 | 8/1982 | Massa | 73/579 |
| 4,380,172 | 4/1983 | Imam et al. | 73/659 |
| 4,408,294 | 10/1983 | Imam et al. | 364/508 |
| 4,559,600 | 12/1985 | Rao | 364/551 |
| 4,628,261 | 12/1986 | Hüschelrath et al. | 364/507 |
| 4,685,335 | 8/1987 | Sato et al. | 73/660 |
| 4,689,993 | 9/1987 | Slettemoen | 73/579 |
| 4,750,134 | 6/1988 | Hüschelrath et al. | 364/507 |
| 4,751,461 | 6/1988 | McWhirter et al. | 364/507 |
| 4,751,657 | 6/1988 | Imam et al. | 364/508 |
| 4,803,639 | 2/1989 | Steele et al. | 364/507 |
| 4,805,457 | 2/1989 | Oates et al. | 73/572 |
| 4,817,016 | 3/1989 | Thompson et al. | 364/507 |
| 4,821,204 | 4/1989 | Hüschlerath | 364/507 |

OTHER PUBLICATIONS

"The Vibrational Behavior of a Turbine Rotor Containing a Transverse Crack", B. Grabowski, *Transactions of the ASME*, vol. 102, Jan. 1980.

Primary Examiner—Parshotam S. Lall
Assistant Examiner—Brian M. Mattson
Attorney, Agent, or Firm—Heslin & Rothenberg

[57] ABSTRACT

The presence, size and location of a crack in a shaft is determined by comparing actual measured natural frequencies of the shaft with the results of an analytical model. From a multistation analytical model of an uncracked shaft, natural frequencies and associated mode shapes are derived. A suspected axial location of a crack is defined and a natural frequency of interest is selected which has an associated mode shape exhibiting maximum deflection at the supected axial location of the crack and at a site of excitation. The analytical model is modified to include a representation of an asymmetric crack, at the suspected crack location, and the predicted split and downward shift of the natural frequency of interest as a function of crack depth is calculated from the modified model. The actual shaft is subjected to a radial excitation force, and vibrational response measurements are taken with an accelerometer along multiple radial directions. A fast Fourier transform analyzer derives a frequency response function from the measurements for each radial direction. The frequency response functions indicate the actual natural frequencies of the shaft. A comparison of these actual natural frequencies with those predicted by the modified model is employed to determine the presence and severity of a crack in the shaft.

20 Claims, 12 Drawing Sheets

Diametrical Inertias of a Cracked Shaft

Frequency Shift as a Function of
Circumferential Position

SHAFT CRACK DETECTION METHOD

BACKGROUND OF THE INVENTION

This invention relates in general to the field of non-destructive testing and more particularly to a method for determining the presence, size and location of a crack in a shaft. For purposes of this description, a crack is defined as any non-designed physical discontinuity and the term shaft encompasses any axially extending structure. Such structures take a wide variety of forms and are employed as motor rotors, shafts of pumps, generators and turbines, bolts and other fasteners, piping, etc. Although the present invention is applicable to any such shafts, it will be presented, by way of example, in the context of detecting a crack in a reactor coolant pump shaft of a pressurized water reactor (PWR).

Nuclear reactors have been operating and producing useful electricity for many years. Within the last few years, several plants have found cracks in the reactor coolant pump shaft near the thermal barrier.

The large reactor coolant pump of a PWR circulates water out of the reactor vessel into steam generators which in turn pass steam to a steam turbine. The reactor coolant pump system consists of a vertical pump with a vertical motor mounted on the pump from above. In a typical design, the entire shaft system hangs vertically and is supported by a thrust bearing located on the top of the vertical motor. The pump system usually has an overhung impeller and an axial suction inlet from below the pump. The cooling water exits the pump through a single radial discharge in the horizontal direction. A net radial force is developed on the rotating shaft during the operation of the pump. This unidirectional unbalanced force applied to the rotating pump shaft can lead to a fatigue crack in the shaft and subsequent pump shaft failure.

The consequences of an unforeseen pump shaft failure can be dire. A nuclear facility can lose as much as $2 million a day in revenues from an unscheduled outage. Further, these pumps are responsible for cooling the reactor, so a failure might lead to a potential melt-down situation and the associated radiation hazard. Since pump shaft replacement is an expensive, time consuming project, it is highly desirable to be able to discover the crack condition early and thus have time to plan and schedule the replacement.

A reliable, early warning method for the identification of shaft cracks, which is relatively easy to implement, is not presently available. Existing devices typically collect and analyze vibrational data off a running machine. However, operating vibrational data in the form of 1X (operating speed) and 2X (twice operating speed) amplitude and phase data is usually clouded with electrical, mechanical and background noise such that little useful information relative to the shaft condition can be obtained.

Field studies show that with existing measurement equipment, cracks are not recognizable until they reach a depth of at least 20% of the shaft diameter. The inability to detect a crack at earlier stages, can leave insufficient time to schedule the manpower, parts, etc. required to replace the shaft.

A critical need thus exists for a reliable, easy to implement shaft crack detection method which can identify the presence, size, and location of a shaft crack in the early stages of crack development. The test method has to be applied on site, in a non-destructive fashion, and with minimal radiation exposure to the test personnel. Further complicating the situation is the fact that only limited access to the reactor coolant pump shaft is available.

SUMMARY OF THE INVENTION

This need is satisfied and the deficiencies of the prior art overcome, in accordance with the principles of the present invention, through the application of a modal analysis test method. By taking advantage of the amplification associated with natural frequencies of the shaft, the new test method is able to identify the presence of a crack having a radial depth on the order of 5% of the pump shaft diameter in the region of the crack. This provides a significantly earlier warning of impending shaft failure than existing techniques, allowing for a planned replacement during a scheduled outage. The new method, when utilized to monitor the shaft for crack initiation and subsequent propagation will enable nuclear power plant operators to avoid difficult shutdown situations and costly unscheduled outages. The test is applied with the shaft at rest, thus avoiding the background noise problems associated with running machine data. Further, the method allows both the external excitation to the shaft, and the response to be obtained through the existing motor stand access holes, without any disassembly, and yet is capable of detecting a crack located anywhere along the axis of the shaft.

The method of the present invention utilizes an analytical model of the shaft under test to guide and interpret the results of a vibrational test applied to the actual shaft. A correlation between the actual natural frequencies exhibited by the shaft in response to a force excitation and a predicted split and shift in a natural frequency of interest provided by the analytical model is used to identify the presence and severity of a crack in the shaft.

In accordance with one aspect of the present invention, a multistation structural dynamics model of an uncracked shaft is employed to derive natural frequencies and associated mode shapes. A probable or suspected axial location of a crack is determined, and a natural frequency of interest is selected having a mode shape which exhibits maximum deflection at the probable axial location of the crack and a site of excitation. The model is then modified to incorporate a representation of an asymmetric crack at the probable axial location, and the resultant split and shift of the natural frequency of interest as a function of crack depth is determined. An excitation force is introduced at the excitation site on a shaft under test and measurements of the shaft's vibrational response along multiple radial directions are taken. The measurements are processed, preferably by a fast Fourier transform analyzer, to determine the actual natural frequencies of the shaft in the region of the frequency of interest. A correlation between these actual natural frequencies and the shift and split in the natural frequency of interest predicted by the analytical model provides an indication of shaft crack presence and severity.

In a further aspect of the invention, the crack is modeled by determining an equivalent diameter and effective length of a right circular section for a stiff axis extending substantially parallel to the crack wave front and a soft axis extending along the depth of the crack. In another aspect of the invention, the analytical model of the shaft can optionally be verified by applying a roving modal analysis to a physical model of the shaft. In a further aspect of the invention, the circumferential location of the crack can be determined by analyzing the frequency response function of the shaft along multiple radial directions.

BRIEF DESCRIPTION OF THE DRAWINGS

These and other objects, features and advantages of the invention will be more readily understood from the following detailed description when read in conjunction with the accompanying drawings, in which.

DETAILED DESCRIPTION

Figure 1:
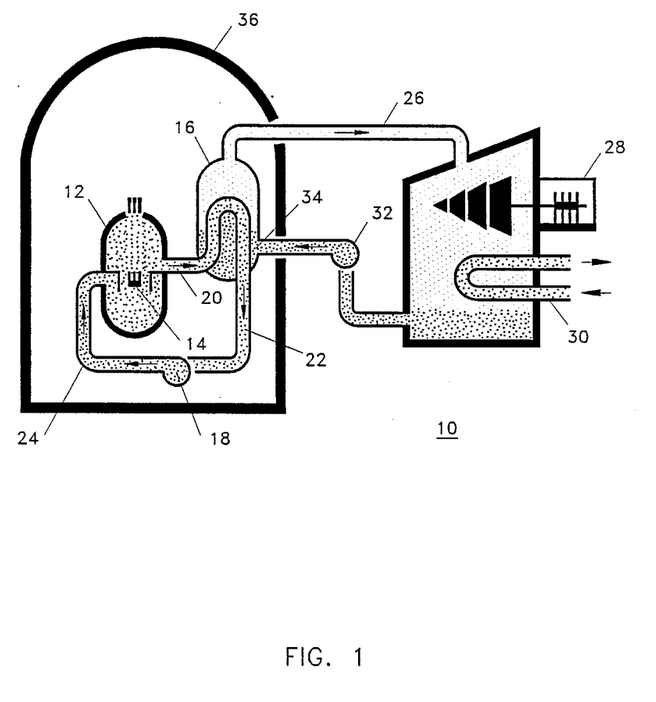
FIG. 1 is a simplified schematic representation of a typical pressurized water reactor (PWR) nuclear power plant.

A schematic of a typical pressurized water reactor (PWR) nuclear power plant 10 is shown in FIG. 1. In operation, high temperature, high pressure water is pumped from the reactor vessel 12 (from around the reactor core 14) to a steam generator (heat exchanger) 16 by the reactor coolant pump 18. A continuous loop of piping 20, 22, 24 interconnects the pressure vessel 12, steam generator 16 and reactor coolant pump 18, as shown. Steam generator 16 in turn passes steam along steam line 26 to a steam turbine generator 28. Finally, cooling water from a condensor 30 is pumped by pump 32 into the inlet 34 of steam generator 16.

Figure 2:
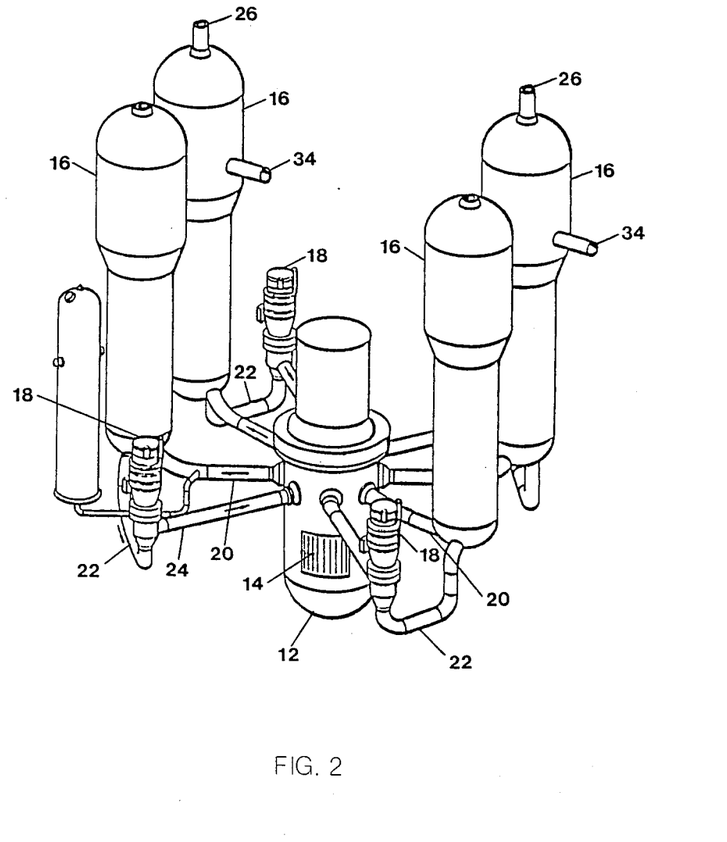
FIG. 2 is a more detailed illustration of a reactor coolant system for a PWR.

FIG. 2 is a more detailed sketch of the reactor coolant system for the PWR which is housed inside the containment structure 36. Four reactor coolant pumps (RCPs) 18 and associated steam generators 16 surround and are interconnected with the reactor vessel 12. If one of the RCPs 18 should fail and be shut down because of a crack in the pump shaft, the nuclear power plant may still be able to operate but obviously at a reduced load and with significantly reduced revenue generated. The present invention relates to an early warning method for detecting shaft cracks which will enable plant operators to avoid unscheduled outages.

Figure 3:
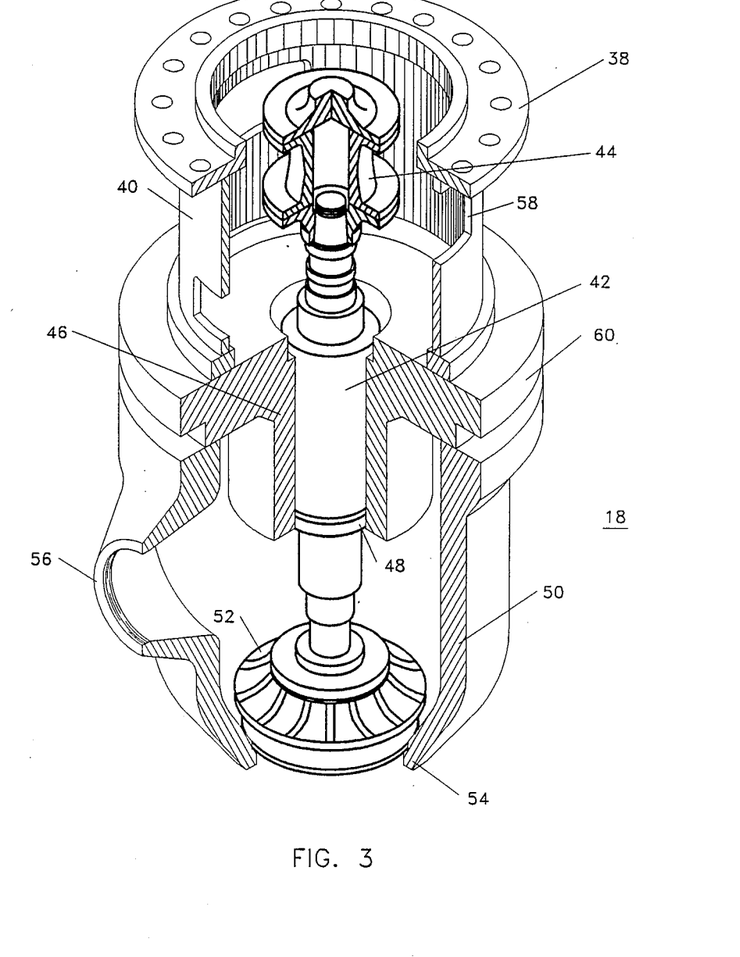
FIG. 3 is a partially broken away sectional view of a reactor coolant pump.

FIG. 3 is a sectional, partially broken away view of a typical reactor coolant pump. A drive motor (not shown) is mounted on flange 38 atop motor support housing 40. The motor's rotor is connected to the pump shaft 42 by a spool piece coupling 44. A radial guide bearing 46 surrounds a portion of pump shaft 42 at a location above a thermal barrier 48. Thermal barrier 48 serves to isolate the bearing area from the extremely high temperatures of the water within casing 50. An impeller 52 is mounted at the lower end of shaft 42 by a set of bolts (not shown).

Water from the steam generator enters vertically upward into the suction nozzle 54 of the reactor coolant pump 18. The pump discharge is horizontal through discharge nozzle 56 into the reactor vessel. During operation of the pump, discharge flow causes a net pressure differential across the pump shaft 42. Since the pump shaft is rotating in the pump casing 50, a given point on the shaft is subjected to a cyclic force. This force is reacted by the pump shaft 42 on the guide bearing 46. Generally the thermal barrier and the guide bearing journal have a sleeve shrunk on the shaft at these locations. In some cases, the sleeve is further secured through the use of a shear pin, or welding, or both locking mechanisms (not shown). The shear pin and welding give rise to stress concentrations which in combination with the cyclic force can result in the formation of a shaft crack, often just below the thermal barrier. Continued operation of the pump will cause the crack to propogate. Shaft cracks have occurred in operating nuclear power plants and have apparently gone undetected until the pump impeller 52 broke off the shaft 42.

The new modal test method of the present invention was developed in order to identify the presence, size and location of a vertical reactor coolant pump shaft crack. The method recognizes that the only access to the shaft system is through the cutouts 58 in the motor support housing 40 which is mounted on the main flange 60 and encloses the coupling 44. No other access to the pump shaft 42 is readily available. The method of the present invention enables both the excitation to the shaft 42, and the response to be obtained through the motor stand access holes 58, without any disassembly.

Figure 4:
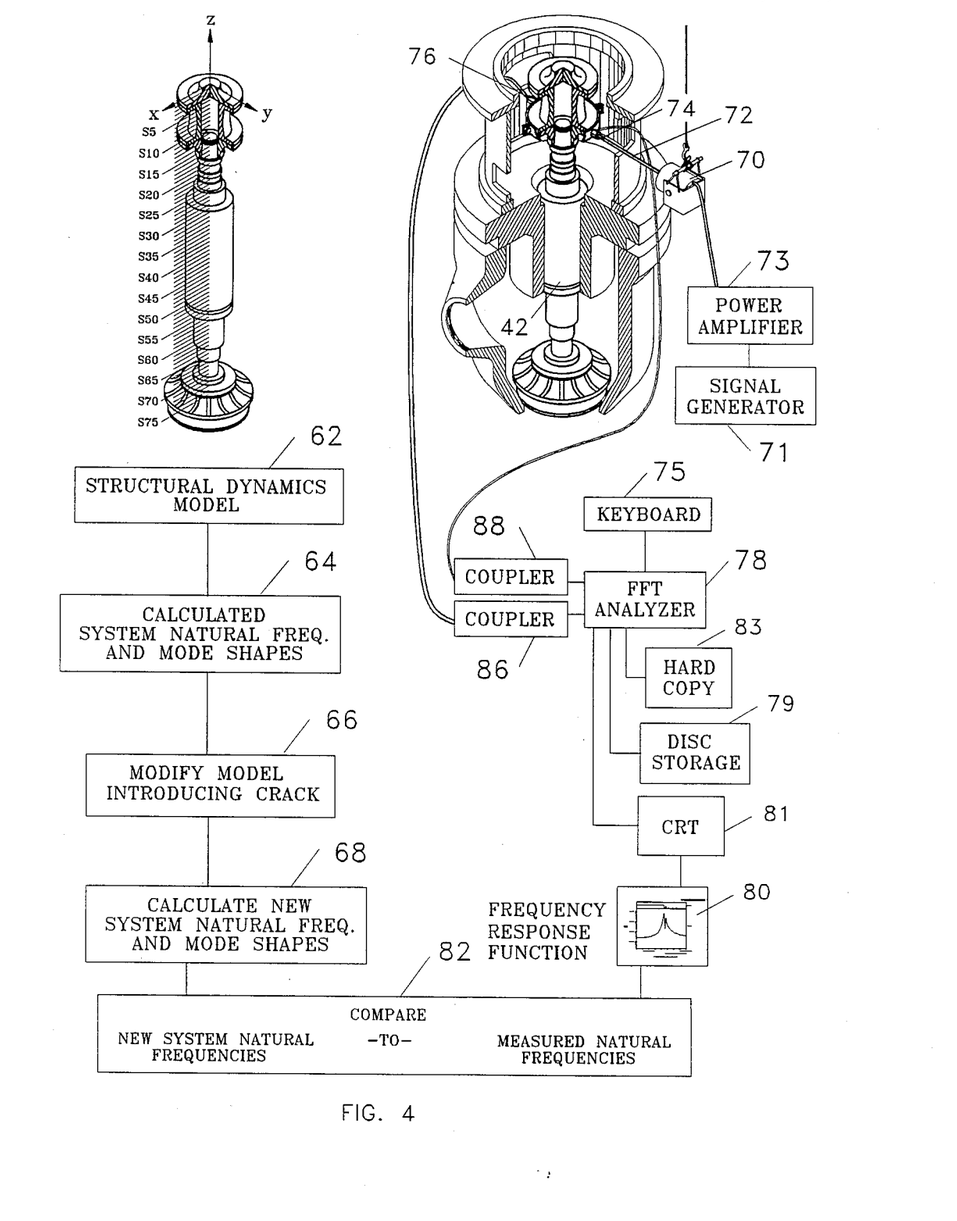
FIG. 4 is schematic depiction, partly in block diagram form, of the general modal analysis test method of the present invention.

FIG. 4 presents an overview of the modal analysis test method of the present invention, as it might be applied to the detection of cracks in a RCP shaft. As shown, a multistation structural dynamics or analytical model 62 of the shaft system, with an uncracked shaft, is developed. From this model, the shaft system's natural frequencies and associated mode shapes are calculated (box 64). The model is then modified by introducing a representation of a crack at a suspected or probable axial location along the shaft (box 66). From the modified model, new system natural frequencies and mode shapes are calculated (box 68). The new natural frequencies reflect a shift and split of the original natural frequencies caused by the introduction of the crack.

Actual or measured natural frequencies of the pump shaft system are determined by introducing a radial force excitation to the stationary pump shaft 42 from electromagnetic shaker 70 through a "stinger" 72 and load cell 74. Shaker 70 is driven by an input excitation signal provided by signal generator 71 through power amplifier 73. The vibrational response of the shaft to the force excitation is measured by an accelerometer 76. Both the excitation and measured response are obtained through the access holes in the motor support housing. Response readings are taken along multiple radial directions and then processed by a fast Fourier transform (FFT) analyzer 78. An input keyboard 75, disc storage device 79, CRT monitor 81, and hard copy printer 83 can be advantageously connected to FFT analyzer 78. The analyzer provides a frequency response function (FRF) 80 which identifies the measured natural frequencies of the actual shaft system. A comparison of these measured natural frequencies with the new system natural frequencies calculated from the modified analytical model is used to determine the presence and severity of cracks in the shaft 42 (box 82).

The method of the present invention is, preferably, applied to the RCP shaft system while the shaft 42 is at rest. This avoids the complications arising from background noise produced by operation of the system. The analytical model identifies a natural frequency of interest based on the axial locations of the suspected crack and the excitation site of the shaft. The modified model further predicts the effect (split and shift) upon the natural frequency of interest by the crack as a function of crack depth. The analytical model thus serves as a road map for guiding the analysis of the actual vibrational test results. Further details and aspects of the method of the present invention will now be described in connection with the remaining drawing figures.

The method of this invention is based on the observation that there is a direct correlation between the existence of a crack and the crack's effect on the shaft system's natural frequencies. A given shaft will have a series of natural or resonant frequencies. If an asymmetric crack is introduced into the shaft, each of the natural frequencies splits into two new, different lower frequencies. The lowest of the new frequencies is associated with a soft axis which extends along the depth of the crack; the other new frequency is associated with a stiff axis substantially parallel to the wave front of the crack. The reduction in value of natural frequency and the separation between the two new frequencies can be correlated with the depth of the crack. The natural frequency most affected by the modeled crack correlates to the axial location of the crack. The circumferential position of the crack can be determined by taking readings in multiple axial directions.

The modal analysis crack detection method of the present invention begins with an accurate multistation analytical model of the shaft or shaft system under test. The analytical model should contain sufficient stations to ensure that the natural frequencies of the shaft can be calculated with a high degree of precision. Preferably, the accuracy provided by such a refined or enhanced model should be comparable to the frequency resolution of the FFT analyzer used in the experimental instrumentation of the shaft. The inventors have discovered that a modeling criteria in which the separation between stations is no greater than the local shaft diameter is desirable.

Figure 5:
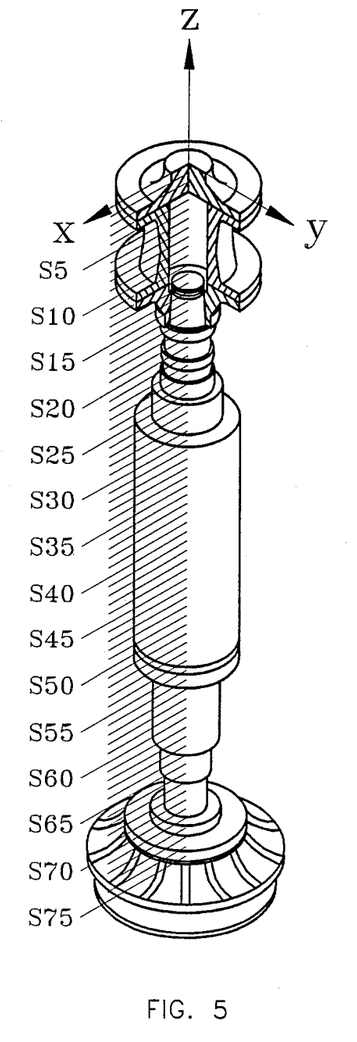
FIG. 5 is a graphical depiction of a multistation structural dynamics model of a pump shaft.

FIG. 5 graphically depicts multiple stations S1-S75 which might be used to model a RCP shaft system. Various rotor dynamics computer programs are publicly available and can be used to model the reactor coolant pump uncracked shaft. Refer, for example, to "DYNAMICS OF DISTRIBUTED PARAMETER ROTOR SYSTEMS: TRANSFER MATRIX AND FINITE ELEMENT TECHNIQUES", a doctoral thesis by R. L. Ruhl, dated January, 1970 and available from University Microfilms, Inc. of Ann Arbor, Michigan as document number 70-12,646; "THE EFFECT OF DISC FLEXIBILITY ON ROTOR DYNAMICS", a doctoral thesis of J. A. Dopkin, dated October 1972 and available from University Microfilms as document number 73-4739; and/or NASA Report No. TN D-7385 "FORTRAN IV COMPUTER PROGRAM FOR CALCULATING CRITICAL SPEEDS OF ROTATING SHAFTS" by R. J. Trivisonno, dated August 1973.

From such computer program models, the natural frequencies and associated mode shapes for the shaft under test can be derived in known fashion. If desired, a physical model of the shaft under study can be constructed and subjected to a roving force modal analysis test to refine and/or verify the computer model predicted natural frequencies and mode shapes.

A suspected or probable axial location of a crack in the shaft under test is then defined. This location is obviously dependent upon the physical forces affecting the shaft in a particular application. As earlier indicated, in a RCP, the expected crack location is in the vicinity of the thermal barrier. A natural frequency of interest is then selected from among the natural frequencies identified by the analytical model. The natural frequency having an associated mode shape which exhibits maximum deflection at both the probable axial location of the crack and the site of excitation of the shaft, is chosen as the natural frequency of interest. The probable axial location of the crack also establishes the diameter D of the shaft for further study.

The new modal test method of the invention was developed so that a shaft system could be examined for a crack when access to the shaft was limited. The method enables regions of the shaft some distance from the excitation point to be examined for cracks. This is accomplished by identifying a higher order natural frequency such that the mode selected has a region of maximum bending near the excitation point and the suspected location of the crack.

Any position along the entire length of the shaft can be examined by using this technique. Each new position will require examining a different natural frequency and associated mode shape. Performing a critical speed analysis of the shaft system allows for an analytical determination of the expected natural frequency of interest, mode shape and region of maximum bending in order to guide the experimental testing of the shaft. The theory underlying the invention will now be briefly discussed.

The nature of a vibrating structure is such that it seeks the state of minimum potential energy. A structure undergoing vibration will dissipate energy through structural damping or hysteresis. It has been found that damping is encountered proportional to displacement but out of phase with the velocity of harmonic oscillation. This phenomenon can be described mathematically by:

$$[m]\ddot{u} + (1 + ig)[K]\ddot{u} = B\sin Wt \quad (1)$$

where
"m" represents mass;
"u" represents displacement coordinate;
"g" is the structural damping coefficient which is usually less than 0.05;
"K" represents shaft stiffness;
"B" represents the magnitude of the forcing function; and
"W" represents angular precession frequency.

The structural damping theory applies to the shaft crack detection method since it is the mechanism responsible for exciting orthogonal, closely spaced natural frequencies. The two orthogonal, primary modes of the cracked shaft, correspond to directions perpendicular to and parallel to the crack "wave front" 84 (see the cross-sectional representation of an asymmetric shaft crack of FIG. 6), and these directions are referred to as the soft axis and stiff axis, respectively.

By exciting the shaft from multiple radial directions, two natural frequencies can be found which are slightly below the natural frequency of interest measured for an uncracked shaft. Their values with respect to circumferential position will indicate the location of the crack. Their frequency separation will be an indication of crack depth, a.

In accordance with the principals of the present invention, the analytical model of the uncracked shaft is modified to include a representation of an assymetric crack at the suspected axial location. The theoretical basis and a preferred approach for so modifying the analytical model will now be discussed.

Figure 7:
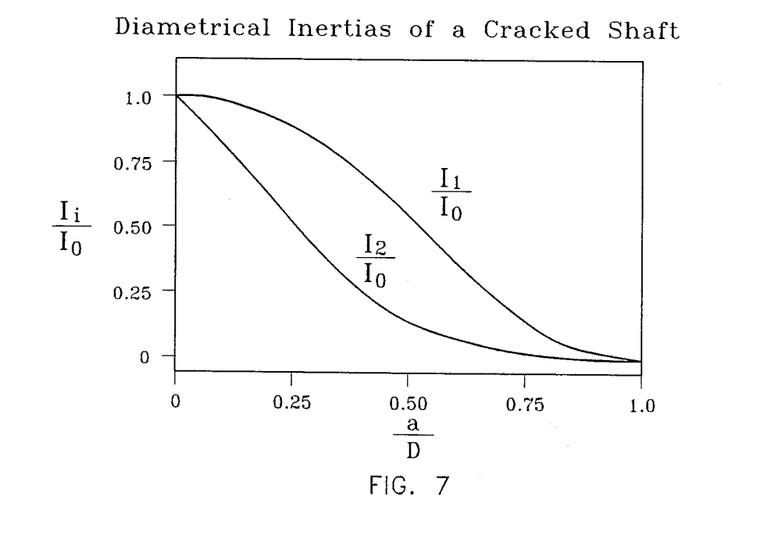
FIG. 7 is a plot of normalized diametrical inertias along stiff and soft axes as a function of crack ratio.

The first step in the preferred method of modeling a shaft crack is to calculate the normalized shaft section inertias for a range of crack depths. Inertia $I_1$, for the stiff direction and inertia $I_2$ for the soft direction are normalized using the inertia $I_0$ for the same diameter shaft uncracked. FIG. 7 depicts a plot of such normalized inertias as a function of crack ratio (crack depth a)/(shaft diameter D).

Figure 6:
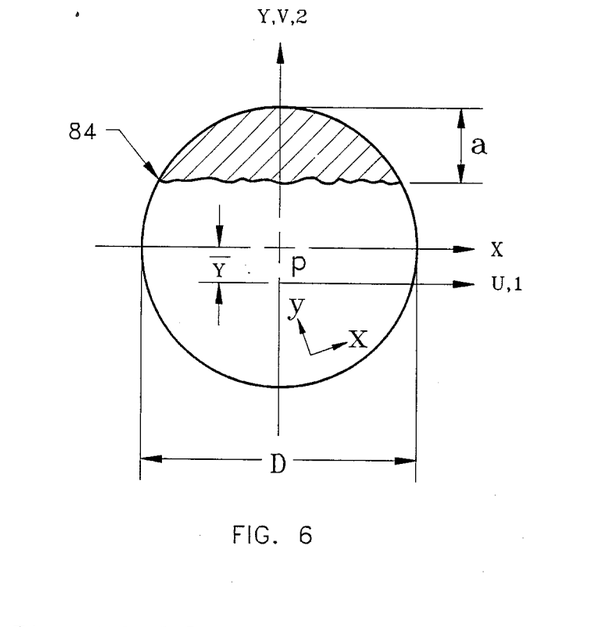
FIG. 6 is a cross-sectional view of an asymmetrically cracked shaft.

The stiffness of a shaft in both torsional and lateral modes is dependent on its section properties, referred to as area second moments or inertias. FIG. 6 depicts a cross section of a cracked shaft. The area inertias can be defined with respect to an arbitary coordinate system [x,y] by the expressions:

$$I_x = \int y^2 dA \quad (2)$$

$$I_y = \int X^2 dA \quad (3)$$

$$I_{xy} = \int XY dA \quad (4)$$

The term Ix relates to stiffness when bending the shaft about the x-axis. Similarly, Iy relates to bending the shaft about the y-axis. Ix and Iy are always positive, but Ixy can be positive, negative, or zero depending upon the orientation and position of the reference axes. The inertia terms are second order tensors, a consequence of which is that $I_x + I_y = C$, where C is a constant for an arbitrary angular orientation of the [x,y] coordinate system.

Refer to the shaft geometry defined in FIG. 6. Let the crack depth be called(a) and the diameter (D). Now construct coordinate system [X,Y] with its origin at the center of the circle representing the uncracked geometry. Rotate [X,Y] such that the Y-axis symmetrically bisects the crack. By definition, the term Ixy will vanish if the cross section is symmetric about at least one axis. Therefore, the product of inertia with respect to the [X,Y] system vanishes, i.e. $I_{XY}=0$.

From classical beam theory, and assuming small deflections, the shaft will bend about its neutral axis. For linear elastic analysis, the neutral axis coincides with the centroidal axis of the section.

As a crack propagates through a shaft, the section neutral axis will migrate in the direction of the crack wave front. At a given crack depth, (a), the neutral axis shifts to point P. A new set of coordinate axes is drawn parallel to [X,Y] and through P. This set of axes is referred to as the Primary Axes [U,V] for the given crack depth. Note that the section is still symmetrial about the V axis, so $I_{UV}=0$. The distance Y between the Points O and P is defined as:

$$\overline{Y} = \int Y dA / \int dA \quad (5)$$

evaluated over the internal region of the cracked section, and with respect to [X,Y].

It is usual to refer to the principal values of section properties, which are the maximum and minimum possible values for $I_u$ and $I_v$, and where $I_{uv}$ must vanish. These properties are usually denoted as $I_1$ and $I_2$ where (with respect to [U,V]):

$$I_1 = \int V^2 dUdV \quad (6)$$

$$I_2 = \int U^2 dUdV \quad (7)$$

$$I_{12} = \int UV dUdV = 0 \quad (8)$$

While the equations (6), (7), and (8) provide a precise mathematical definition of the Second Area Moments, evaluation of the integrals as defined can be tedious, even for the simple cracked shaft geometry. It can be shown that the inertia terms with respect to a given set of axes can be evaluated with respect to a second set of axes:

$$I^{[UV]} = I^{[XY]} + Ad^2 \quad (9)$$

where:

$I^{[UV]}$ = Inertial components with respect to primary axes [UV] \quad (10)

$I^{[XY]}$ = Inertial components with respect to centroidal axes [XY] \quad (11)

where, [X,Y] is parallel to [U,V]
A = Area of cross section
d = Distance between parallel axes (X,U) for $I_V$ or (Y,V) for $I_U$.

For the conditions shown in FIG. 6, (d) corresponds to the distance between the X and U axes, or:

$$d = \overline{Y} \quad (12)$$

Now it can be stated that the principal second moments are:

$$I_1 = I_U = I_X + A\overline{Y}^2 \quad (13)$$

$$I_2 = I_V = +A(0)^2 = I_Y \quad (14)$$

where:

$$I_X = \int Y^2 dX dY \quad (15)$$

$$I_Y = \int X^2 dX dY \quad (16)$$

It is still necessary to evaluate the expressions for $I_X$ and $I_Y$ on the domain by the cracked shaft. The above integrals can be solved using a summation of integrals over continuous subdomains:

$$I(X,Y) = I^1(X,Y) + I^2(X,Y) + I^3(X,Y) \quad (17)$$

where:

$$I^1(X,Y) = \int_{-R}^{t} \int_{-W(X)}^{W(X)} (\quad) dY\,dX \quad (18)$$

$$I^2(X,Y) = \int_{-t}^{t} \int_{-W(X)}^{h} (\quad) dY\,dX \quad (19)$$

$$I^3(X,Y) = \int_{t}^{R} \int_{-W(x)}^{W(X)} (\quad) dY\,dX \text{ and,} \quad (20)$$

$$W(x) = (R^2 - X^2);\ t = a(D - a);\ R = d/2;\ h = R - a$$

This technique, while mathematically precise is usually inconvenient. Therefore, a summation of components is used which states that:

$$I_x = \sum_i (I_{x^i} + A^i y_i^2) \quad (21)$$

$$I_y = \sum_i (I_{y^i} + A^i x_i^2) \quad (22)$$

where:
$Ix_i, Iy_i$ are second moments with respect to component centroids
$A^i$ = area of component, positive or negative
$x_1, y_i$ = distance from [X,Y] system to component's centroidal coordinate system.

In summary, the principal second moments for the cracked shaft are computed using the parallel axis theorem and method of components. The area and centroidal distances $Y_i$ change with varying crack depth, necessitating many calculations. A computer program can be utilized to evaluate the expression over the range of interest. A single pair of curves can be generated in dimensionless form to represent all cases. The results of these calculations are shown in FIG. 7.

The next step in the preferred manner of modeling the shaft crack is to calculate an equivalent right circular diameter $D_{eq}$ for each shaft section inertia in each direction, i.e. along the soft and stiff axes, in accordance with the following relationships:

$$D_{eqx} = \sqrt[4]{\frac{I_x \cdot 64}{\pi}} \quad (23)$$

$$D_{eqy} = \sqrt[4]{\frac{I_Y \cdot 64}{\pi}} \quad (24)$$

An effective length L representing the axial extent of the shaft effected by the crack is then computed in accordance with the following formula:

$$L = 2(a)(\tan 53°) \quad (25)$$

Figure 8:
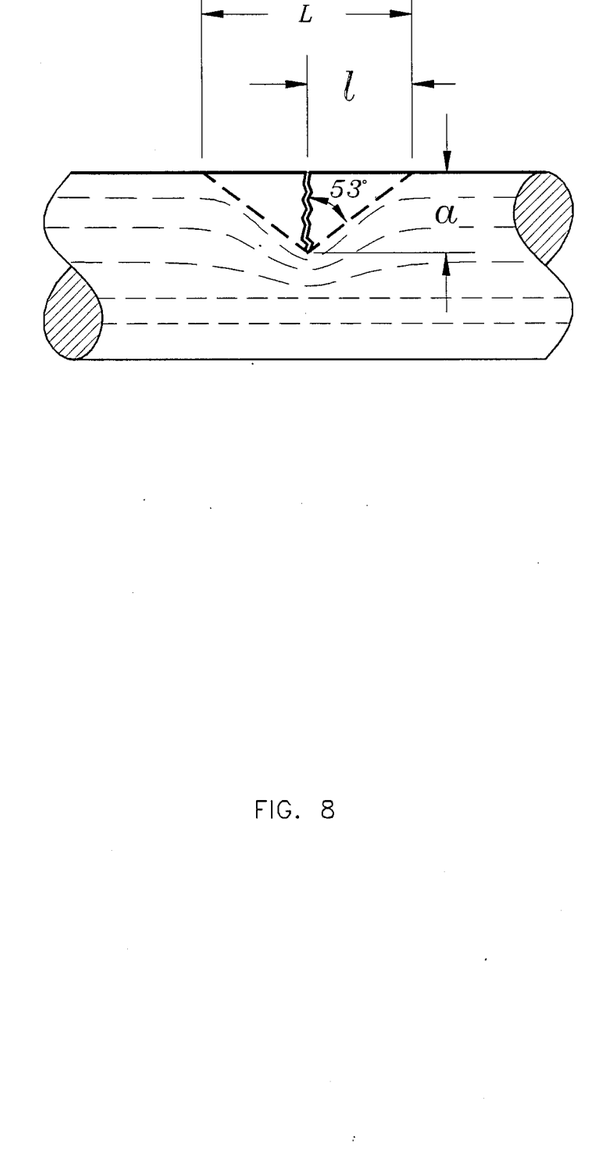
FIG. 8 is a schematic illustration of the lines of stress associated with a shaft crack and the dimensions used to calculate the effective length when modeling an asymmetric crack.

The effective length relationship is illustrated in FIG. 8 and the theory underlying this approach is described in a paper by B. Grabowski entitled "The Vibrational Behavior of a Turbine Rotor Containing a Transverse Crack", Transactions of the ASME Journal of Mechanical Design, Vol. 102, pp. 140-146, January 1980. A range of angles could be used to determine the effective length but 53° appears to provide good results.

The original structural dynamics model of the shaft structure is modified at the suspected axial location of the crack using the equivalent diameter and effective length for the stiff and soft axes. From this modified model, the shaft new natural frequencies and mode shapes for each direction, for a range of crack depths, can be derived and a plot of the new natural frequencies as a function of crack ratio (a/D) made.

Figure 9:
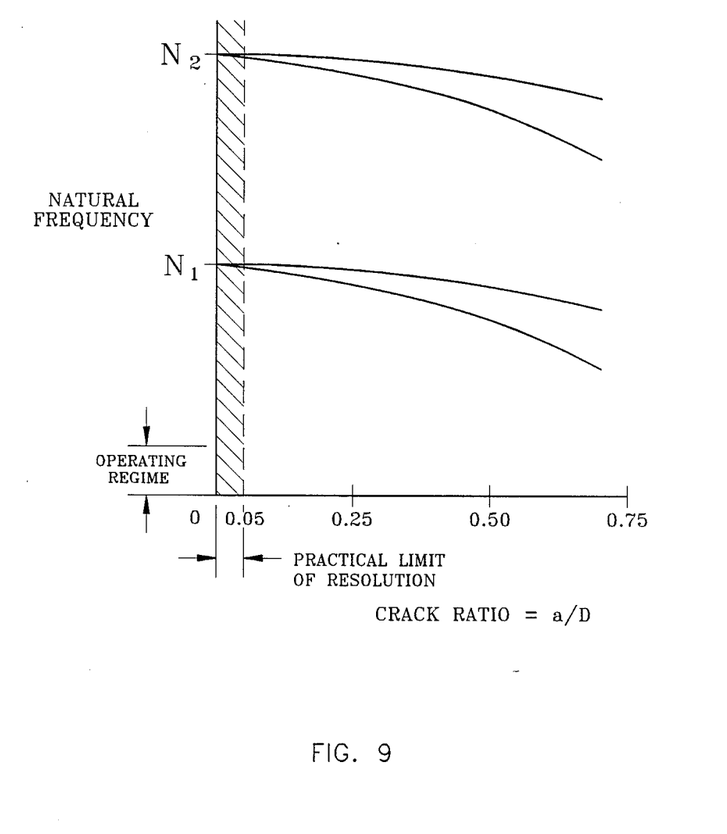
FIG. 9 is a plot illustrating the downward shift and split of shaft natural frequencies as a function of crack ratio.

FIG. 9 presents such a plot for two natural frequencies $N_1$ and $N_2$. The effect of the modeled crack on other natural frequencies could similarly be plotted. Natural frequencies for the uncracked shaft are plotted along the abscissa, and crack ratio is plotted along the ordinate in FIG. 9. As shown, the natural frequencies are substantially higher than the operating regime of the RCP, as would be expected with a well designed machine. Cracks having a depth on the order of 5% or less of the local diameter are considered to be below the practical limit of resolution because of the lack of simultaneous mass and stiffness homogenity in the real world. Beyond a crack ratio of 0.05, the map of FIG. 9 indicates the predicted split and shift of the natural frequencies caused by the introduction of the crack in the model. As the severity of the crack increases, the spread between the two new frequencies becomes more pronounced. The calculated shift and split of a natural frequency of interest for a particular suspected axial location of a crack, as derived from the modified model, can be correlated with actual natural frequency measurements taken on the shaft to determine the presence and size of cracks in the shaft.

Figure 10:
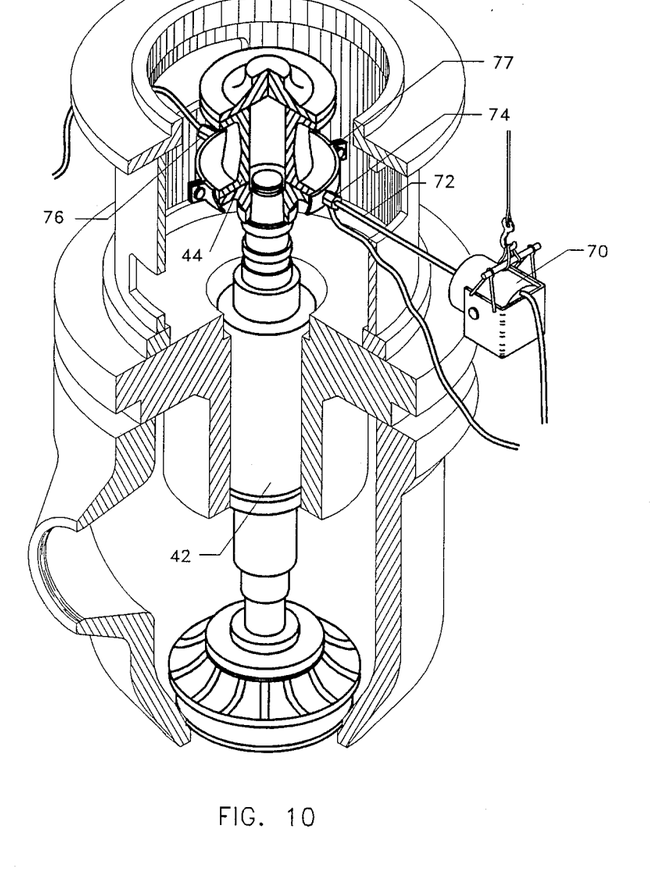
FIG. 10 is a partially cut-away sketch of an exemplary reactor coolant pump shaft test instrumentation arrangement.

FIG. 10 illustrates exemplary test equipment which can be used to measure the actual natural frequencies of shaft 42 of the RCP. The shaft is excited radially using an electromagnetic shaker 70 connected to the coupling 44 by a stinger 72, i.e. a thin cylindrical rod. A load cell 74 measures the input force and provides an electrical signal representative thereof. The vibration response of the shaft is preferably measured by an accelerometer 76 located diametrically opposite from the stinger 72. This 180° relationship is desirable since it maximizes resolution and avoids cross effects. A rotatable collar 77, to which load cell 74 and accelerometer 76 can be attached, can be advantageously employed to quickly change the radial direction of measurement.

Figure 11:
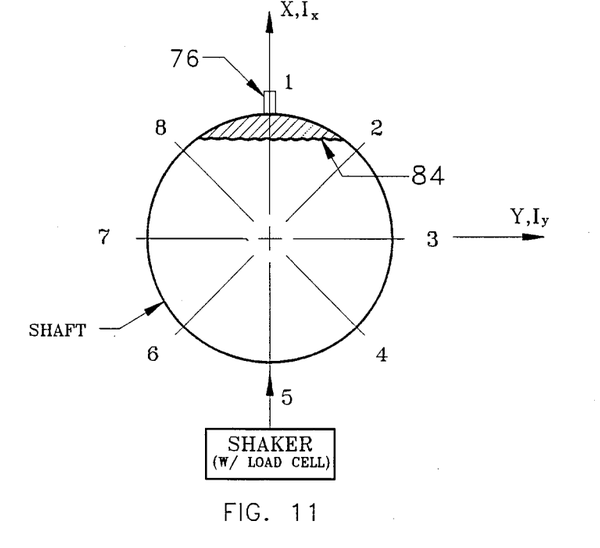
FIG. 11 illustrates how the vibrational response measurements on the shaft are taken along multiple radial directions.
Figure 12:
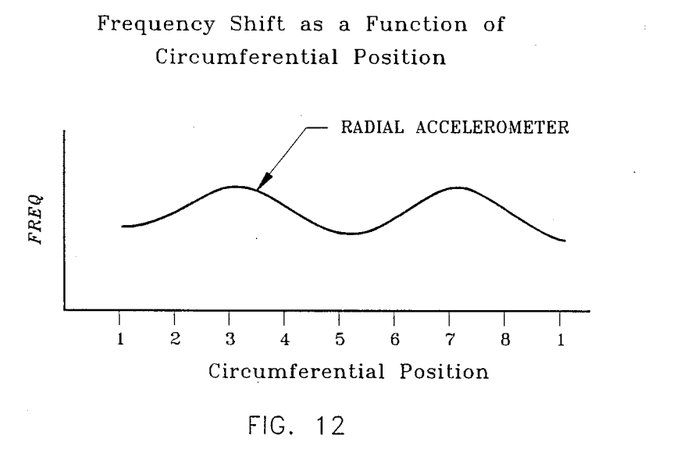
FIG. 12 is a plot of frequency shift as a function of circumferential position.
Figure 13A:
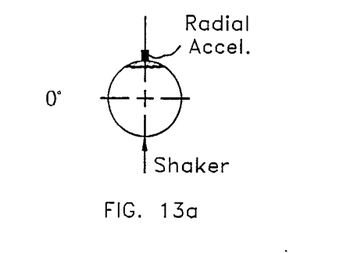
FIGS 13a, 13c, 13e and 13g depict four radial directions of measurement
Figure 13B:
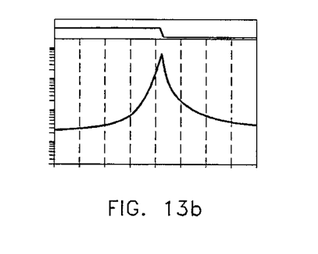
FIGS. 13b, 13d, 13f and 13h present a graph of frequency response function for a respective one of said four different radial directions.
Figure 13C:
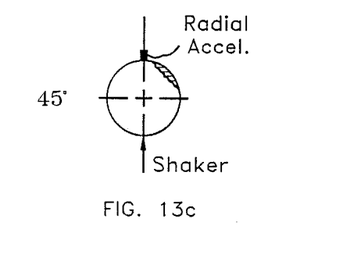
Figure 13D:
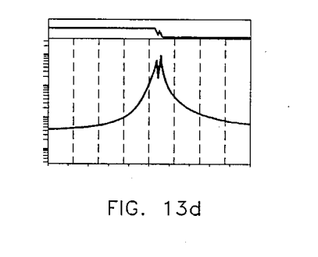
Figure 13E:
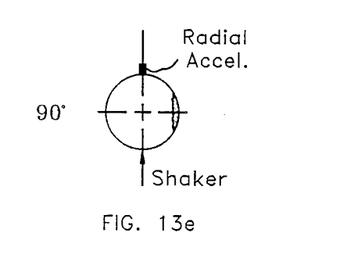
Figure 13F:
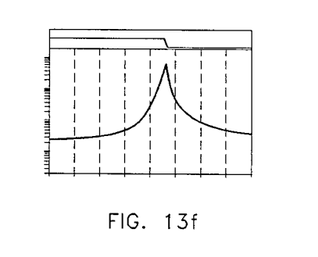
Figure 13G:
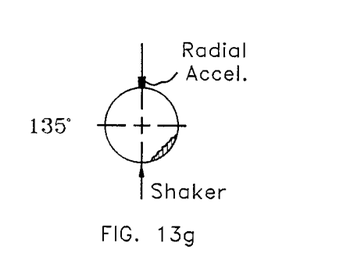
Figure 13H:
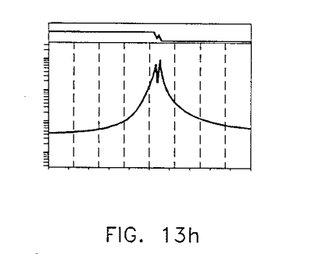

The output signals from accelerometer 76 and load cell 74 are fed through suitable couplers 86, 88 respectively, as shown in FIG. 4, to a FFT analyzer 78. The analyzer, in known fashion, provides a frequency response function, the peaks of which represent the actual natural frequencies. By exciting the shaft and measuring the system response in several predefined radial directions around the shaft (see FIG. 11), one can observe the variation of the shaft natural frequencies as a function of circumferential position (see FIGS. 12 and 13). In FIGS. 13a-13h the graphs on the right side of the drawing sheet represent the frequency response function for the associated angular direction illustrated on the left side of the sheet. Each peak in an FRF signifies a measured natural frequency. At the 0° position (FIGS. 13a and 13b) the actual natural frequency associated with the soft axis is exhibited. At the 90° position (FIGS. 13e and 13f) the measured natural frequency associated with the stiff direction is presented. As would be expected, the natural frequency in the stiff direction is somewhat higher than that in the soft direction. At intermediate angular positions (FIGS. 13c and 13 d; 13g and 13h), both natural frequencies are detected.

Referring again to FIG. 10, it will be seen that for a shaft of a RCP, a driving point modal analysis is employed (i.e. the input is applied and the output measured at the same axial location) because of the limited accessibility to the shaft. In other applications of the method of the present invention, the excitation site and response measuring position may be axially displaced.

Various known equipment can be used to implement the experimental portion of the method of the present invention. As an example, the following test equipment could be used to perform the cracked shaft modal testing:

1. A Zonic 6081Z Four Channel Analysis System With a Zoom Option, Signal Generator Option and Modal Analysis Software. The Zonic 6081Z multichannel FFT signal processor provides four channels for real time data acquisition with a 40 KHz signal range. The digital zoom analysis processor enables a 20u Hz frequency resolution. The system has a built in 15 megabyte Winchester disk drive and a 320 Kilobyte 3.5 inch micro floppy disk for data back up and storage. The signal generator option provides for user selectable wave forms with either linear or logarithmic sweep rates. Sine, Triangle, or Square wave forms can be selected from 1 Hz to 40 KHz. Random noise is possible from DC to 40 KHz. Programmable bursting of any wave form is selectable including band limited white noise. The burst noise output provides decreased test time and reduced leakage errors.

2. MB Dynamics Modal 50 Electromechanical Shaker With a model 2250 Power Amplifier. The MB Dynamics Modal 50 Electromechanical Shaker has been especially designed for modal testing. The shaker can be easily suspended for quick alignment with the test piece. The power amplifier model 2250 amplifies the input excitation signal from the Zonic Signal Generator to drive the shaker. An inertial mass can be attached to the suspended shaker to react against the excitation force.

3. Kistler Instrument Corporation 1 Volt/G Accelerometer (0.5 to 5000 Hz Range), 5516 Coupler; 9712 A50, 501b. force transducer, 99.2 mV/lb; 5120 coupler with DC offset adjustment for use with the force transducer.

By comparing the actual natural frequencies in the region of the frequency of interest, with the new system frequencies predicted by the modified model (FIG. 9), the presence and severity (i.e. extent of cross sectional reduction as indicated by crack ratio) at the suspected axial location can be determined. Analysis of the FRFs at the various radial directions (see FIG. 13) reveals the circumferential location of the crack. Obviously, the test method can be employed in an iterative fashion to check for cracks at different axial locations. Similarly, the method can be applied over time to monitor crack propagation.

Figures 14, 14A:
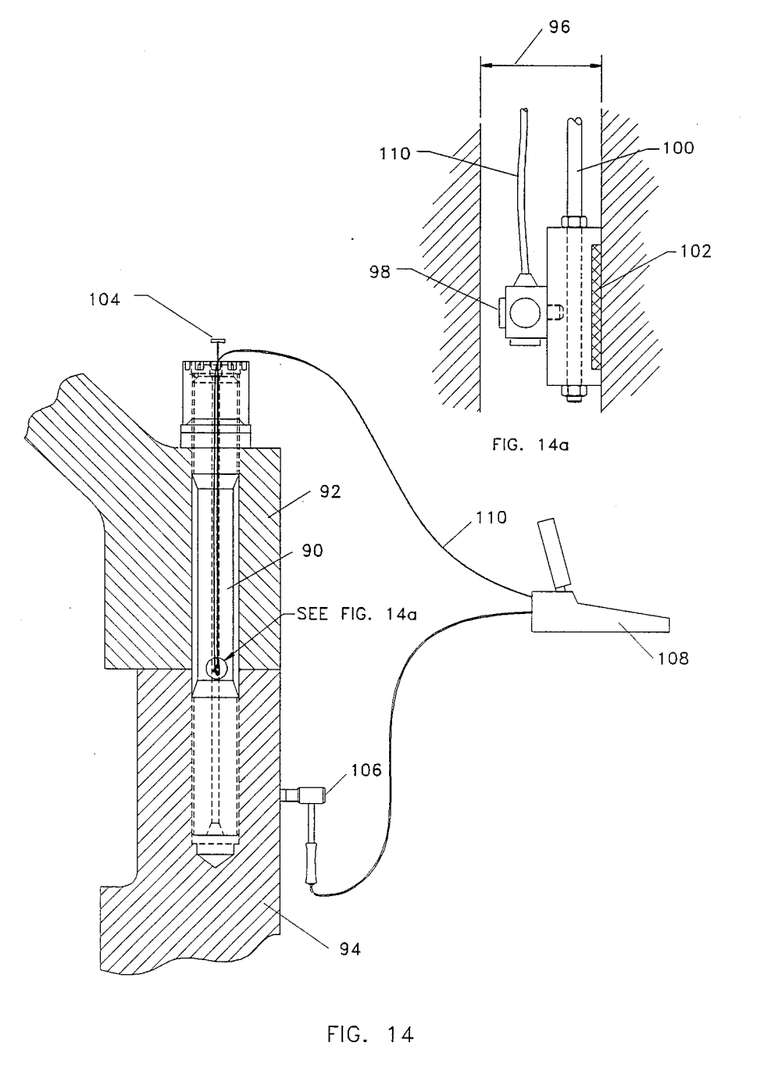
FIG. 14 schematically illustrates how the method of the present invention can be advantageously employed to detect a crack in a bolt that holds the lid on a nuclear reactor vessel.
FIG. 14a is a blown-up detailed view of a portion of FIG. 14.

The method of the present invention can be applied to shafts having orientations other than vertical (e.g. horizontal) and to symmetrical structures other than rotors and rotatable shafts. FIGS. 14 and 14a illustrate application of the method to a bolt 90 used to secure a lid 92 to a reactor vessel base 94. The bolt contains an axially extending bore 96 in which an accelerometer 98 can be selectively located by a positioning rod 100 and secured by a magnet 102 at a suspected crack location. A positioning handle 104 connected to rod 100 facilitates positioning of the accelerometer 98 within the bore 96.

The bolt is excited to resonance by a hammer fitted with a force transducer 106 connected to FFT analyzer/computer 108. A vibration response measurement from accelerometer 98 is fed to FFT analyzer 108 via cable 110. The FFT analyzer can, in known fashion, indicate the actual natural frequencies of the bolt 90 in the region of a natural frequency of interest for comparison of these measured natural frequencies with predicted natural frequencies derived from a modified analytical model of the bolt in the manner hereinabove described.

A similar approach can be used to identify cracks in a horizontal turbine shaft having a central bore and other similar structures. It is expected that the method can also be extended to detect cracks in bolts mounting an impeller to the bottom of a shaft of a RCP.

From the foregoing description, it will be apparent that a new method for detecting cracks in shafts has been developed which provides earlier detection than prior approaches. The new method allows for the identification of the presence, size and location of a crack anywhere along the shaft even when access to the shaft is limited. The method is preferably performed with the shaft at rest and is applicable to a wide variety of structures.

Although several presently preferred embodiments of the invention have been described and depicted, it will be apparent to those skilled in this art, that various modifications, substitutions, additions, etc. can be made without departing from the spirit of the invention, the scope of which is defined by the claims appended hereto.

What is claimed is:

1. A method for detecting a crack in a shaft under test, comprising the steps of:
    utilizing a multistation structural dynamics model representative of the shaft under test without cracks to derive natural frequencies of an uncracked shaft, each natural frequency having an associated mode shape, representative of shaft deflection at the natural frequency;
    defining a probable axial location of a crack and selecting from among the natural frequencies derived from the model a natural frequency of interest having an associated mode shape which exhibits maximum deflection at said probable axial location of the crack and at a site of excitation;
    modifying the model to include a representation of a crack at said probable axial location;
    employing said modified model to calculate effect of said representation of a crack upon the natural frequency of interest as a function of crack depth;
    introducing an excitation force at an excitation site on the shaft under test and taking measurements of vibrational response of the shaft to said force along multiple directions;

processing said measurements to determine actual natural frequencies of the shaft under test in a region near the natural frequency of interest; and comparing said actual natural frequencies to the calculated effect of the representation of a crack upon the natural frequency of interest in order to determine existence and severity of a crack in the shaft under test.

2. The method of claim 1 wherein the modifying step comprising modifying the model to include a representation of an asymmetric crack having a wave front extending parallel to a stiff axis and a crack depth extending along a soft axis; and wherein said step of employing the modified model to calculate the effect of the representation of a crack upon the natural frequency of interest comprises calculating a downward shift and a split in the natural frequency of interest as a function of a ratio of crack depth to shaft diameter at said probable axial location.

3. The method of claim 2 wherein said model modifying step comprises representing said crack as a right circular section having an equivalent diameter and effective length for each of said soft axis and said stiff axis.

4. The method of claim 3 wherein said modifying step comprises:

calculating shaft section inertia for a range of crack depths at the probable axial location for the stiff axis and for the soft axis; calculating an equivalent right circular diameter for each shaft section inertia along each of said axes, in accordance with the following equation:

$$D_{eq} = \sqrt[4]{\frac{I \cdot 64}{\pi}}$$

where

"$D_{eq}$" represents the equivalent diameter of a right circular section for a specified axis, and "I" represents the shaft section inertia for a specified axis;

and computing the effective length in accordance with the following equation:

$$L_{[eq]} = 2(a)(\tan 53°)$$

where

"$L_{[eq]}$" represents the effective length and

"a" represents the crack depth.

5. The method of claim 2 wherein said step of defining a probable axial location of a crack comprises identifying the shaft location at which cracks tend to develop as a result of forces acting on the shaft in accordance with an intended use of the shaft.

6. The method of claim 2 wherein the step of taking measurements of vibrational response comprises measuring acceleration of the shaft.

7. The method of claim 6 wherein the step of introducing an excitation force comprises imparting random white noise force excitation to the shaft.

8. The method of claim 6 wherein the step of introducing an excitation force comprises imparting band limited vibrational energy in the region of the natural frequency of interest to the shaft.

9. The method of claim 6 wherein acceleration is measured by an accelerometer, the excitation force is introduced by an electromagnetic shaker through a stinger and load cell, and wherein output signals from the accelerometer and load cell are provided to an FFT analyzer.

10. The method of claim 2 wherein said processing step comprises determining a frequency response function along each of said multiple directions with a fast Fourier transform analyzer.

11. The method of claim 10 wherein frequency resolution of the natural frequencies derived from the multistation structure dynamics model of the shaft is at least as great as frequency resolution of the fast Fourier transform analyzer.

12. The method of claim 2 wherein the distance between adjacent stations of the structural dynamics model is no greater than the local shaft diameter.

13. The method of claim 2 wherein access to the shaft under test is limited and the excitation force is introduced and the response measurements taken at a common axial location on the shaft.

14. The method of claim 2 wherein the measurements of vibrational response are taken at a location which corresponds to the probable axial location of the crack.

15. The method of claim 2 further comprising the step of verifying the natural frequencies and associated mode shapes derived from the structural dynamics model by subjecting an actual shaft to a roving force modal analysis.

16. The method of claim 2 further comprising the step of determining circumferential location of a crack in the shaft under test by analyzing the actual natural frequencies of the shaft along said multiple directions.

17. The method of claim 2 wherein the shaft comprises a rotatable shaft which is subjected to said excitation force while the shaft is at rest.

18. The method of claim 2 wherein said shaft has a hollow longitudinally extending central bore and the measurements of vibrational response are taken from within said bore.

19. The method of claim 18 wherein said shaft comprises a bolt.

20. A method for detecting a crack in a shaft under test, comprising the steps of:

employing a multistation analytical model of the shaft to determine a natural frequency of interest for a crack at a designated location and to predict a split and shift of said natural frequency of interest as a function of crack depth;

measuring actual natural frequencies of the shaft under test at rest in response to a vibration inducing force excitation, said actual natural frequencies being in the region of the natural frequency of interest; and comparing said actual natural frequencies to the predicted split and shift of the natural frequency of interest to determine a correlation therebetween, whereby such a correlation indicates existence of a crack in a shaft and severity thereof.

* * * * *